United States Patent [19]
LaFleur

[11] 4,280,230
[45] Jul. 28, 1981

[54] DISPOSABLE TRAINING PANTIES

[76] Inventor: Ruby S. LaFleur, 10490 W. Outer Dr., Detroit, Mich. 48223

[21] Appl. No.: 60,688

[22] Filed: Jul. 25, 1979

[51] Int. Cl.$^3$ ............................................. A41B 9/04
[52] U.S. Cl. .......................................... 2/408; 2/406
[58] Field of Search ................... 2/408, 406, 407, 111

[56] References Cited

U.S. PATENT DOCUMENTS

| 2,719,976 | 10/1955 | Sussman | 2/408 X |
| 3,154,082 | 10/1964 | Cape | 2/408 X |
| 3,279,469 | 10/1966 | Schustack | 2/408 X |
| 3,599,640 | 8/1971 | Larson | 2/406 X |
| 3,974,836 | 8/1976 | Carlson | 2/408 X |

FOREIGN PATENT DOCUMENTS

| 848372 | 7/1939 | France | 2/408 |
| 1464572 | 2/1977 | United Kingdom | 2/406 |

Primary Examiner—H. Hampton Hunter

[57] ABSTRACT

Training panties for babies and toddlers, the panties being made in several different designs, one of the designs including a cotton panty with cut-out crotch, a disposable paper crotch member insertable therein and easily attached in place by Velcro-like members of the pantie being hooked in holes of the paper member, the Velcro-like members being hidden behind flaps that keep wetness away from the child's body.

1 Claim, 10 Drawing Figures

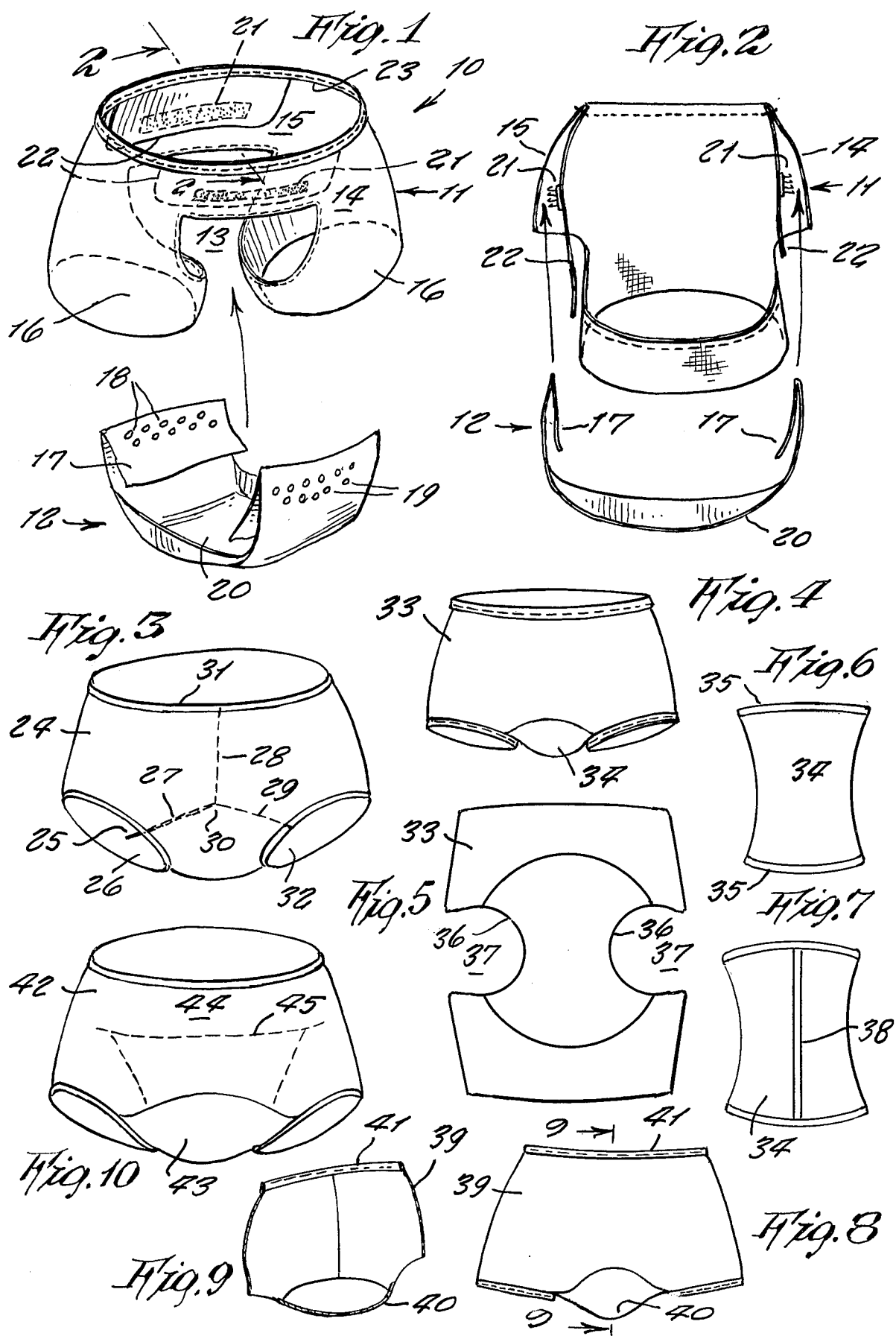

DISPOSABLE TRAINING PANTIES

This invention relates generally to training pants for very young children, before they learn to control urination.

It is well known, that this lack of control results in the necessity of frequent laundering, and a large supply of such panties during this age of a child.

A principal object of the present invention is to provide a training panty, which, accordingly, in various designs has a portion thereof which is disposable, so as to be replaceable, thus eliminating the large amount of laundering.

Another object is to provide a training panty, which, in another design, is completely disposable by being inexpensively made of paper.

Still another object is to provide a training panty, which, in one design, is used for beginner training, and which, in another design, is used for advanced training.

Other objects are to provide a training panty, which is simple in construction, easy to put on and to remove.

These, and other objects, will be readily evident, upon a study of the following specification, and the accompanying drawing, wherein:

FIG. 1 is a perspective view of one design of beginner training panty in which the crotch is a disposable paper tucked from underneath into the cotton panty, and using a Velcro-like single member for quick and easy hooking in holes in the paper for holding it up under plastic-coated cotton flaps that prevent the wet paper from contacting the body in this area for greater comfort;

FIG. 2 is a cross-sectional view thereof, on line 2—2 of FIG. 1;

FIG. 3 is a disposable training panty having a string to pull open the crotch;

FIG. 4 shows a cotton panty with disposable crotch insert;

FIG. 5 shows a construction of the panty of FIG. 4;

FIG. 6 shows an inside view of a disposable pad thereof;

FIG. 7 shows the outside view thereof;

FIG. 8 is a panty made of paper, and having a thick crotch of several layers of paper;

FIG. 9 is a cross-sectional view, on line 9—9 of FIG. 8, and

FIG. 10 is another design of cotton panty for beginner training, having a flap and crotch that opens in front for reclosing.

Referring now to the drawing in greater detail, and more particularly to FIGS. 1 and 2 thereof, at this time, the reference numeral 10 represents a training panty, according to the present invention, wherein there is a soft cotton pants member 11, and a disposable paper crotch insert 12, that fits in a cut-out crotch opening 13 of the member 11, and which cuts away a lower portion of front and rear panels 14 and 15, as well as crotch portions of legs 16. The crotch 12 has folded-over front and rear ends 17, having perforated holes 18 punched out, together with holes 19 in a central panel 20 thereof, so as to receive hooks of a Velcro-type member 21, fastened to outer sides of flaps 22, for quick and easy attachment. The hooks of member 21 generally comprise short stiff plastic bristles which are hook shaped at their ends. The flaps are made of a soft cotton on an inner side, and which is either plasticized on its outer side, or else has a plastic film attached thereto. The flaps are placed inside member 11, and stitched thereto along front and rear sides of elastic waist-band 23. In use, the flaps keep a wetted crotch member 12 from wetting the child's body at the front or rear, while lying down, such as when asleep. Changing a soiled crotch member is made quick and easy, because the pants member 11 need not be removed, nor even to be lowered, and the large crotch opening permits easy cleaning of the baby buttocks.

FIG. 3 shows a disposable training panty 24, wherein a pull string 25 conveniently extends out a leg opening 26, so as to be pulled for tearing open the crotch for easy removal of the panty. The string 25, stitched to the panty, comprises a strand 27 of two individual string members 28 and 29, which, at point 30, separate, and one is stitched up to the waist-band 31, while the other is stitched on the other leg to the leg opening 32.

In FIGS. 4 to 7, a panty 33 is made of cotton, and has a disposable crotch insert 34, made of a paper pad. The insert is attached to the panty by means of adhesive tapes 35, on opposite inside edges of the insert, for attachment to curved edges 36 of panty notches 37. An adhesive tape 38 extends transversely across the center of the insert outer side.

In FIGS. 8 and 9, a panty 39, made of paper, has a crotch insert 40 made of several layers of paper, so as to be thick and extra absorbent for extended length use, at such times as, for example, when not at home, and a change is not as convenient to accomplish. An elastic tape 41, around a top edge of the panty, forms the waistband.

In FIG. 10, a beginner training cotton panty 42 has a crotch flap 43, that opens at the front of the panty, and is then reclosable again, the flap being insertable behind the panty front panel 44, up to a location indicated by dotted lines 45, so as not to fall down readily.

Thus, several constructions of the invention are herewith presented.

While various changes may be made in the detail construction, it is understood that such changes will be within the spirit and scope of the present invention, as is defined by the appended claims.

What I now claim is:

1. A training panty for babies and toddlers, comprising, in combination, a panty member including front and rear panels, an endless waistband around upper edges of said panels, and a pair of downward legs at the sides of said panels, with openings therethrough, and a crotch member between said legs; said crotch member comprising a separate paper insert that is fitted in a crotch opening at a crotch of said panty member; opposite ends of said insert being supported between each of said panels and a downward, depending flap secured to an inner side of each said panels; each of said crotch inserts comprising a control panel, and a folded-over front extension and a folded-over rear extension at opposite ends thereof, a plurality of perforated holes punched out through each said front and rear extensions, and also through opposite ends of said control panel, a loop pile fastener secured to an outward side of each said flaps, and said loop pile fastener comprising a plurality of stiff plastic bristles having hooked ends hooked through said perforated holes of said insert.

* * * * *